United States Patent [19]

Kirchhoff et al.

[11] Patent Number: 4,783,514

[45] Date of Patent: * Nov. 8, 1988

[54] POLYMERIC MONOARYLCYCLOBUTANE COMPOSITIONS

[75] Inventors: Robert A. Kirchhoff; Alan K. Schrock; Stephen F. Hahn, all of Midland, Mich.

[73] Assignee: The Dow Chemical Company, Midland, Mich.

[*] Notice: The portion of the term of this patent subsequent to Feb. 9, 2005 has been disclaimed.

[21] Appl. No.: 872,372

[22] Filed: Jun. 9, 1986

Related U.S. Application Data

[63] Continuation-in-part of Ser. No. 835,013, Feb. 28, 1986, Pat. No. 4,724,226, which is a continuation-in-part of Ser. No. 644,849, Aug. 27, 1984, abandoned.

[51] Int. Cl.[4] .............................................. C08F 10/00
[52] U.S. Cl. .................................... 526/281; 526/284; 526/285; 526/279

[58] Field of Search ............... 526/281, 284, 285, 279; 556/489; 585/27; 546/112

[56] References Cited

U.S. PATENT DOCUMENTS

| | | | |
|---|---|---|---|
| 4,540,763 | 9/1985 | Kirchhoff | 526/281 |
| 4,622,375 | 11/1986 | Wong | 526/284 |
| 4,667,004 | 5/1987 | Wong | 526/284 |
| 4,667,005 | 5/1987 | Wong | 526/284 |

OTHER PUBLICATIONS

Patterson, A. M., Capell, L. T. and Walker, D. F.: The Ring Index (Second Edition), American Chemical Society (1960), Ring Structure 833, p. 114.

Primary Examiner—Joseph L. Schofer
Assistant Examiner—Peter D. Mulcahy

[57] ABSTRACT

Polymeric compositions are comprised of, in polymerized form, a monomer which contains one reactive arylcyclobutane moiety.

18 Claims, No Drawings

POLYMERIC MONOARYLCYCLOBUTANE COMPOSITIONS

CROSS-REFERENCE TO RELATED APPLICATIONS

This is a continuation-in-part of copending U.S. patent application Ser. No. 835,013, U.S. Pat. No. 4,724,226 filed Feb. 28, 1986, which is a continuation-in-part of copending U.S. patent application Ser. No. 644,849, filed Aug. 27, 1984 abandoned.

BACKGROUND OF THE INVENTION

This invention relates to polymers prepared from monoarylcyclobutane monomers.

Thermoset resins are compositions which can solidify irreversibly upon heating. Such resins are useful in many engineering applications such as, for example, coatings, structural laminates, adhesives, films, composites and the like. Examples of conventional forming techniques are transfer molding, compression molding and hand-laying processing.

Desirable thermoset resins possess chemical resistance, tensile strength, temperature resistance, electroinsulative or electroconductive properties and other properties which encourage their use as engineering materials. Such properties depend on the chemical structural of the resin or materials added to the resin. For example, resins comprised of aromatic structures, especially aromatic polyamides and polyimides intrinsically possess thermal and oxidative stability. Unfortunately, the preparation and curing of such resins require the handling of highly toxic and volatile compositions. Furthermore, the resins are difficult to form in molding processes and are at times undesirably insoluble in many organic solvents.

Another class of engineering polymeric compositions are thermoplastic polymeric compositions. Such compositions soften upon heating and can be formed into many useful shapes. Upon cooling, the composition is hardens to desired shapes. Advantageously, the polymeric compositions exhibit chemical resistance and are structurally durable. Examples of suitable thermoplastic polymeric compositions are those prepared from polycarbonate thermoplastic compositions.

In U.S. Pat. No. 4,540,763, poly(arylcyclobutene) polymers are disclosed. Such polymers are prepared from monomers which contain at least 2 arylcyclobutene moieties per monomer. The polymers exhibit excellent mechanical and physical properties such as high strength, thermal stability and glass transition temperatures. Unfortunately, because of the thermosetting nature of the polymers, the polymers are difficult to process in compression molding processes.

It would be desirable to have a new class of polymeric compositions which could exhibit the thermosetting or thermoplastic properties and which could be polymerized with thermosetting polymers to impart processing advantages such as compression molding capabilities.

SUMMARY OF THE INVENTION

This invention is a polymeric composition comprising, in polymerized form, a monomer containing one reactive arylcyclobutane moiety.

In another aspect, this invention is a method of forming solid polymeric parts. The process comprises subjecting a monomer containing one arylcyclobutane moiety to polymerization conditions, which conditions include the application of molding pressure.

The polymeric compositions of this invention can exhibit thermosetting or thermoplastic properties. Also, the compositions can be copolymerized with thermosetting polymers, such as polyarylcyclobutanes, to impart compression molding properties to such polymers. The polymeric compositions are especially useful in providing solid polymeric parts which can be employed in electronics applications, such as in the preparation of laminates for printed circuit boards, and as encapsulation or passivation resins.

DETAILED DESCRIPTION OF THE INVENTION

The monomers employed in preparing the polymeric compositions of this invention contain one arylcyclobutane moiety. Such monomers shall be referred to as monoarylcyclobutenes. The polymeric compositions can be homopolymers of one monoarylcyclobutane monomer, copolymers of at least 2 monoarylcyclobutane monomers, or copolymers of at least one monoarylcyclobutane monomer and at least one polyarylcyclobutane monomer (i.e., a monomer which contains at least two reactive arylcyclobutane moieties). The polymeric composition can also be comprised of certain fillers or reinforcing materials, such as inorganic or organic powders; inorganic and polymeric fibers such as glass or polyimide type fibers and the like. Such reinforcement materials are especially desirable in preparing laminates for circuit boards.

An arylcyclobutane moiety is an aryl moiety which contains one or more cyclobutane rings fused to the aromatic ring. The arylcyclobutane moieties are reactive when they are in a position such that under ring-opening conditions, addition polymerization sites can be formed. Aryl moieties are those compounds referred to as aromatic compounds containing $(4N+2)\pi$ electrons as described in Morrison & Boyd, *Organic Chemistry*, 3rd ed., 1973. Suitable aromatic moieties include benzene, naphthalene, phenanthrene, anthracene, pyridine, biaryl moieties, and two or more aromatic moieties which are bridged by alkylene or cycloalkylene moieties. Preferred aromatic moieties are benzene, naphthalene, biphenyl, binaphthyl, diphenyl alkene, and diphenylcycloalkene moieties. The most preferred aromatic moiety is benzene. The aryl moiety can be further substituted with a variety of electron-donating and electron-withdrawing moieties, which will be further defined. The monoarylcyclobutane monomers correspond to the formula

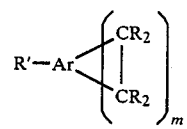

wherein Ar is an aryl moiety; R is, separately and independently, hydrogen, an electron-donating moiety or an electron-withdrawing moiety; R' is a molecular group, an m is an integer of at least one.

Because the cyclobutane ring can form polymerization sites under ring-opening conditions, the molecular group, R', can be any organic or inorganic moiety. The molecular group can be inert under ring-opening conditions (i.e., does not contribute or participate in the polymerization) or it can contain a group which is reactive under ring-opening conditions. Such a reactive group can be reactive toward the open cyclobutane rings, or it can be reactive with other like groups on the molecular group. The particular molecular group can affect the properties of the polymers. Typically, to impart thermoplastic properties, the molecular group, R', is an alkenyl group.

Preferred monoarylcyclobutane monomers contain an unsaturated alkyl group in the molecular group. When the unsaturated alkyl group is an alkenyl group, the monomers can be represented by the formula

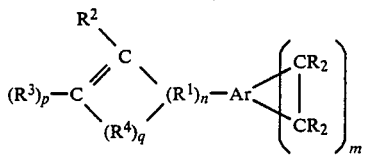
II wherein
Ar is an aryl moiety;
R, $R^2$ and $R^3$ are separately and independently in each occurrence hydrogen, an electron-donating moiety or an electron-withdrawing moiety;
$R^1$ and $R^4$ are a polyvalent organic moiety or a polyvalent inorganic moiety;
m is an integer of at least 1;
n is an integer of 0 or 1;
p is an integer of 1 or 2; and
q is an integer of 0 or 1 provided that when n is 0, then the alkenyl group is directly bonded to the aryl moiety, q is 0, and p is 2; and when p is 2, then q is 0.

Separately and independently in each occurrence means that R, $R^2$ and $R^3$ can be different in each occurrence.

Preferably, q=0, p=2, and the monomers can be represented by the formula:

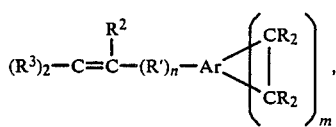
III wherein Ar, R, R', $R^2$, $R^3$, m and n are as defined above.

Preferred compounds corresponding to Formula II include compounds that, when n is 0 or 1, q is 0 and p is 2, the molecular group can be a 1,2-alkenyl moiety wherein $R^1$ is an alkyl group when n is 1. In another preferred compound, the molecular group can be a 1-aryl-alkenyl group, wherein n is 0 or 1, q is 0, p is 2 and at least one $R^3$ is an aromatic moiety. In yet another preferred compound, the molecular group contains a heteroatom, n is 1 and $R^1$ contains the heteroatom, q is 0 or 1 and p is 1 or 2. The molecular group can be a heterocyclic ring containing an ethylenically unsaturated group.

Preferred unsaturated alkyl monoarylcyclobutane monomers, wherein the unsaturated alkyl group is an alkynyl group can correspond to the formula

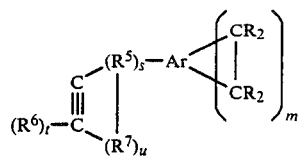
IV wherein
Ar, R, and m are defined as above;
$R^6$ is a hydrogen, an electron-donating moiety, or an electron-withdrawing moiety;
$R^5$ and $R^7$ are a polyvalent organic moiety, or a polyvalent inorganic moiety;
s, is an integer of 0 or 1;
t is an integer of 0 or 1; and
u is an integer of 0 or 1; provided that when s is 0 then the alkynyl group is bonded directly to the aryl moiety, u is 0 and t is 1; when t is 1, then u is 0; and when u is 1, then s is 1, and t is 0.

Preferably, u=0, t=1, and the monomers can correspond to the formula

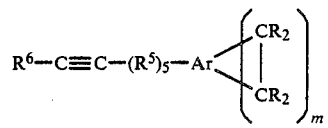
V wherein Ar, R, $R^5$, $R^6$, s and m are as defined above.

Polyvalent inorganic moiety refers to any inorganic moiety which can bond to two or more other moieties. Such polyvalent inorganic moieties can be covalently or ionically bonded to the other moiety. Examples of polyvalent inorganic moieties include oxygen, phosphorus, phosphorus oxide, sulfur, nitrogen, silicon, polysiloxanes, polyvalent metals, sulfoxide, sulfone, a polyvalent metal bound to a polyvalent oxygenated moiety wherein the polyvalent oxygenated moiety can be further bound to an aryl moiety (for example, a polyvalent carboxylate salt). Preferred polyvalent inorganic moieties include oxygen, sulfur, silicon, polysiloxanes, and polyvalent metals bound to polyvalent oxygenated moieties.

The polyvalent organic moiety can be any polyvalent organic moiety bonded to two or more other moieties. The organic moiety can also contain one or more heteroatoms, such as oxygen, nitrogen, phosphorus, silicon or sulfur, or an organic moiety containing one or more aromatic moieties. Preferably, the polyvalent organic moiety is an alkyl poly-yl which is bonded to functionalized linking groups or an alkyl poly-yl which contains an aromatic moiety. Alkyl poly-yl is an alkyl moiety which is bonded to two or more linking groups, wherein the alkyl poly-yl can further contain one or more of the hereinbefore defined heteroatoms. Included within the term alkyl are any organic moieties containing carbon and hydrogen atoms. Suitable alkyl groups include the following organic moieties: alkanes, alkenes, alkynes, cycloalkanes, cycloalkenes, aromatic moieties wherein aromatic is as defined hereinbefore, alkyl-substituted aromatic moieties, and aryl-substituted aliphatic moieties.

Electron-donating moieties are molecular or atomic groups which donate electrons more than a hydrogen atom would if accompanying the same site. Electron-withdrawing moieties are groups which more readily withdraw an electron relative to a hydrogen atom. Examples of suitable electron-withdrawing moieties include —NO₂, —CN, Br, I, Cl, F, —PR₂, —CO₂H, —CO₂R,

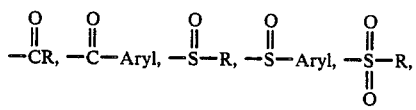

and aryl. Examples of suitable electron-donating groups include alkyl, aryl, alkoxy, aryloxy, hydrocarbyl, hydrocarbyloxy, hydrocarbylthio, —OH, —OR, —NH₂, —NHR, —NR₂. Hydrocarbyl refers to any organic moiety containing carbon and hydrogen atoms; hydrocarbyloxy refers to such organic moieties which further contain a hydroxyl moiety; and hydrocarbylthio refers to organic moieties which further contain a sulfur atom.

Preferably, the arylcyclobutene moiety is a benzocyclobutane moiety, wherein the aryl moiety, Ar, is a benzene moiety. The preferred alkenyl monoarylcyclobutanes can correspond to the formula

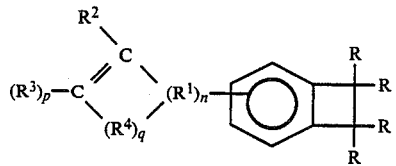

wherein R, R¹, R², R³, R⁴, n, q and p are defined above, and m is 1.

The preferred alkynyl monoarylcyclobutane monomers correspond to the formula

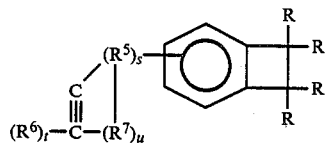

wherein R, R⁵, R⁶, R⁷, s, t, and u are defined above; and m is 1. More preferably, u=0, and the alkynyl group is part of a molecular chain rather than a cyclic molecular group. The chain form is more stable.

A preferred ethylenically unsaturated monoarylcyclobutane monomer is an N-substituted arylcyclobutyl-unsaturated cyclic imide, which corresponds to the formula

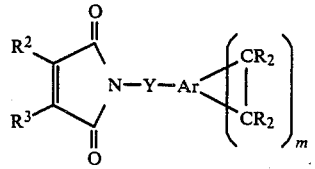

wherein
Ar is an aromatic moiety;
R is separately in each occurrence hydrogen or an electron-withdrawing group;

R² and R³ are separately in each occurrence hydrogen, a hydrocarbyl, hydrocarbyloxy or hydrocarbylthio group;
Y is a direct bond or a divalent organic moiety; and
m is an integer of at least 1.

Formula V corresponds to Formula II as follows: Ar, R, R² and R³ are the same in both formulae; R¹ in Formula II is

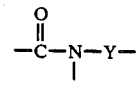

in Formula VIII; R⁴ in Formula II is

in Formula VIII; n is 1, p is 1, and q is 1 in Formula VIII.

A more preferred embodiment is the N-substituted benzocyclobutyl-unsaturated cyclic imide, which corresponds to the formula

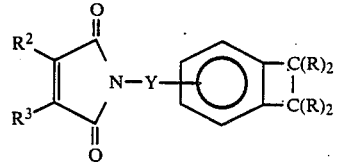

wherein R² and R³ are separately in each occurrence hydrogen, hydrocarbyl, hydrocarbyloxy or carbonitrile hydrocarbylthio; and
Y is a direct bond or a divalent organic or inorganic moiety.

Preferred molecular groups are ethylenically unsaturated groups and aromatic moieties bridged by ethylenically unsaturated groups to the arylcyclobutane moiety. Preferably, the ethylenically unsaturated group is a vinyl group. When the arylcyclobutane is benzocyclobutane, the preferred monomers correspond to the formulae

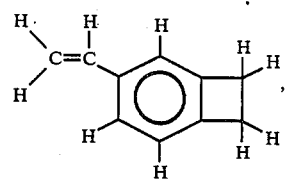

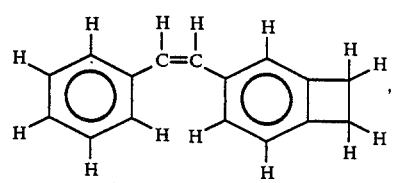

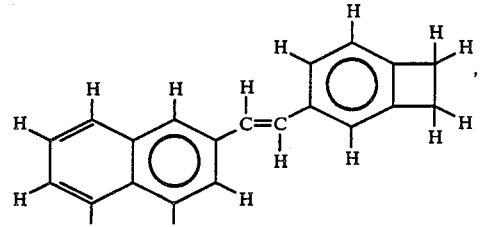

XII

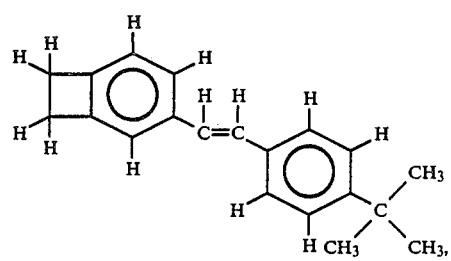

XIII

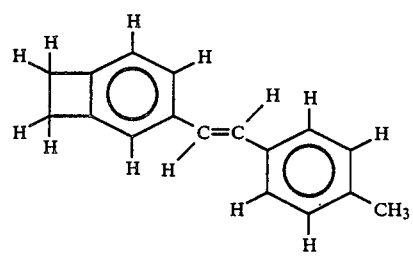

XIV

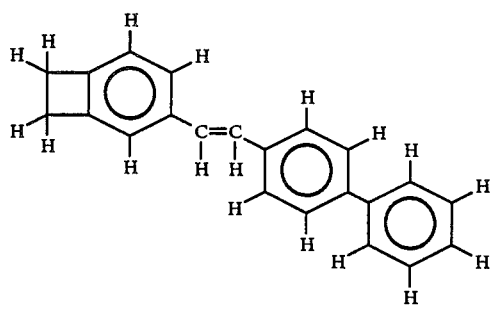

XV

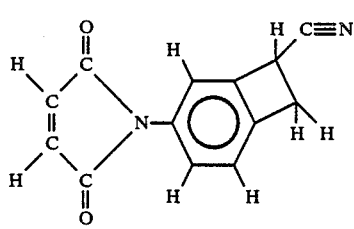

XVI

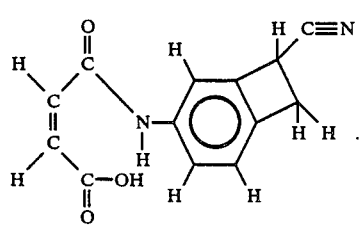

XVII

Examples of other preferred monoarylcyclobutane monomers include 4-naphthyl-benzocyclobutane, which corresponds to the formula

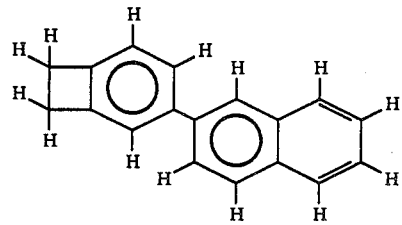

XVIII

Another preferred compound is phenyl-cyclobutyl benzoate.

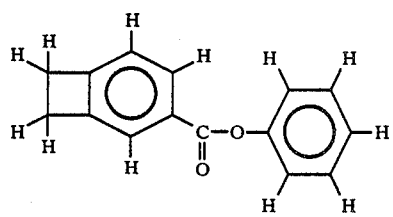

XIX

Still yet another preferred compound is an acetamido-cyanato-benzocyclobutane.

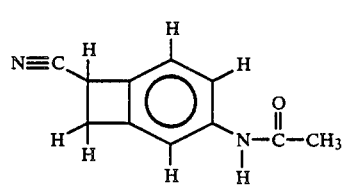

XX

A more preferred alkynyl monoarylcyclobutane is 1-trimethylsily-2-(4-benzocyclobutyl) acetylene, and corresponds to the formula

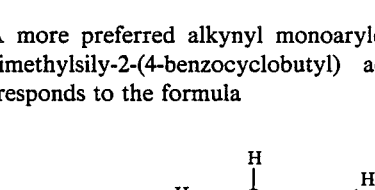

XXI

This formula corresponds to the general Formula VII as follows:

R in Formula VII is H in Formula XXI; m in Formula VII is 1 in Formula XXI; s in Formula VII is 0 in Formula XXI and therefore $R^5$ in Formula VII is not present in Formula XXI and the alkynyl group is bonded directly to the aryl moiety; u in Formula VII is 0 in Formula XXI, and therefore $R^7$ is not present; t in Formula VII is 1, and $R^6$ in Formula VII is

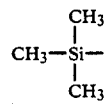

in Formula XXI.

Another preferred alkynyl monoarylcyclobutane is 1-(4-benzocyclobutyl)-2-phenyl acetylene which corresponds to the formula

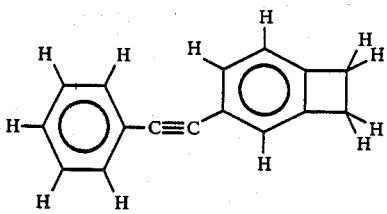
                                                                                                        XXII This formula corresponds to the general Formula VII as follows:

R in Formula VII is H in Formula XXI; m in Formula VII is 1 in Formula XXII; s in Formula VII is 0 in Formula XXII and therefore R⁵ in Formula VII is not present in Formula XXII and the alkynyl group is bonded directly to the aryl moiety; u in Formula VII is 0 in Formula XXII and therefore R⁷ is not present in Formula XXII; t in Formula VII is 1, and R⁶ in Formula VII is

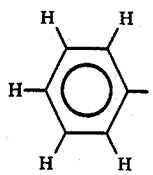

in Formula XXII.

The monomeric compositions of this invention can be prepared by reacting a suitably substituted arylcyclobutane compound with a molecular group containing a moiety reactive with the substituted arylcyclobutane. A variety of synthesis schemes are suitable, and examples are disclosed in U.S. Pat. Nos. 4,540,763, 4,562,280, and 4,570,011, all herein incorporated by reference.

Typically, the unsaturated alkyl monoarylcyclobutane monomers of this invention can be prepared by reacting a brominated arylcyclobutane compound with a molecular compound containing an unsaturated alkyl group. An arylcyclobutane compound can be brominated by dissolving an arylcyclobutane in acetic acid and contacting a brominating agent of pyridinium perbromide hydrobromide in the presence of mercuric salts, for example, mercuric acetate, at a temperature of between about 20° C. and about 50° C. The brominated product can be recovered by extraction and distillation.

The brominated arylcyclobutane can be converted to an arylcyclobutane compound containing a different reactive substituent such as a carboxylic acid, ester, amine, amido, and the like. Such substituted arylcyclobutane compounds can be reacted with molecular compounds containing correspondingly reactive substituents. An amine substituted arylcyclobutane can be reacted with a compound which contains at least one anhydride moiety to prepare an arylcyclobutane monomer containing a cyclic imide linking group. Also, a carboxylate-substituted arylcyclobutane compound can be contacted with a compound containing an amine moiety to prepare an arylcyclobutane monomer containing an amido-linking group. Further, the bromo-substituted arylcyclobutane compound can be contacted with a compound containing a terminal unsaturated alkyl moiety (i.e., an alkenyl or alkynyl moiety) to prepare an arylcyclobutane monomer with an alkenyl or alkynyl molecular group substituted on the aryl moiety. Also, an ester substituted arylcyclobutane can be contacted with a primary aliphatic amine in a suitable diluent in the presence of heat to prepare an arylcyclobutane monomer with an amido aliphatic molecular group substituted on the aryl moiety.

A preferred compound, 4-vinylbenzocyclobutane (Formula X), can be prepared by contacting an amount of 4-bromobenzocyclobutane with ethylene in a pressurized reactor in the presence of a palladium (II) acetate catalyst and a cocatalyst such as tri-o-tolylphosphine, and an appropriate base. After a suitable reaction temperature and time, 4-vinylbenzocyclobutane can be extracted in a suitable solvent.

To prepare the preferred monomer, 1-phenyl-2-(4-benzocyclobutyl)ethene (Formula XI), an amount of 4-bromobenzocyclobutane is contacted with styrene in the presence of a palladium catalyst, a suitable diluent and a suitable base under a nitrogen atmosphere at reflux. The product can be recovered from an aqueous acid solution.

To prepare the preferred monomer, 1-naphthyl-2-(4-benzocyclobutyl)ethene (Formula XII), an amount of 4-bromobenzocyclobutane is contacted with an amount of vinylnaphthalene in the presence of a suitable catalyst at sufficient reaction temperatures.

To prepare the preferred monomer, 1-p-tert-butyl-phenyl-2-(4-benzocyclobutyl)ethene (Formula XIII), an amount of 4-bromobenzocyclobutane is contacted with an amount of para-tertiary butylstyrene in the presence of a suitable catalyst at sufficient reaction temperatures.

To prepare the preferred monomer of an arylcyclobutyl unsaturated cyclic imide (Formula XVI), a cyclic anhydride is contacted with an amine-substituted arylcyclobutane under conditions to form an arylcyclobutylamido alkenoic acid. The acid can be dehydrated to cyclize the amidoalkenoic acid into a cyclic imide ring and form the N-substituted arylcyclobutyl unsaturated cyclic imide (Formula XVI).

To prepare the preferred monomer, 1-trimethylsilyl-2-(4-benzocyclobutyl)acetylene, (Formula XXI) equal molar amounts of trimethylsilyl acetylene and 4-bromobenzocyclobutane are contacted in the presence of a suitable catalyst mixture. Suitable catalyst mixtures can comprise metal catalysts. Preferably, the catalyst mixture comprises catalytic amounts of bistriphenylphosphine palladium (II) chloride, triphenyl phosphine, and cuprous iodide. The arylcyclobutane and acetylene compounds are preferably added to the catalyst mixture in the presence of a suitable solvent. A preferred solvent is triethylamine. The reaction can be conducted at reflux for a suitable reaction time.

The preferred monomer 1-(4-benzocyclobutyl)-2-phenyl acetylene (Formula XXII) can be prepared in a similar manner, with phenyl acetylene being substituted for the trimethylsilyl acetylene.

Unsaturated alkyl heterocyclic arylcyclobutane monomers can be prepared according to similar methods. For example, methods for preparing cyclobutapyridines and substituted cyclobutapyridines are disclosed by J. M. Riemann, and W. S. Trahanovsky in *Tetrahedron Letters*, No. 22, pp. 1867–1870, 1977 (cyclobuta[b]pyridine and cyclobuta[c]pyridine); and by W. D. Crow, A. N. Khan; and M. N. Paddoa-Row in *Australian Journal of Chemistry*, No. 28, pp. 1741–1754, 1975 (2-methylcyclobuta[b]pyridine). Methods suitable for preparing other subsituted cyclobutapyridines are suggested in the following references for the indicated compounds: in *Organic Reactions*, Vol. I, p. 91 (2-aminocyclobuta[b-

]pyridine); in *Berichte*, No. 57, p. 791, and p. 1802, 1924 (2-hydroxycyclobuta[b]pyridine is prepared from 2-aminocyclobuta[b]pyridine); by Hatinger and Lieben in *Monatschaft*, No. 6, p. 279, 1885, and Rath, *Annalan Chemische*, NO. 486, p. 71, 1931 (2-bromocyclobuta[b]pyridine is prepared from 2-hydroxycyclobuta[b]pyridine); and by Hatinger and Lieben, in *Monatschaft*, No. 6, p. 279, 1885 and by Rath in *Annalan Chemische*, No. 486, p. 71, 1931 (2-chlorocyclobuta[b]pyridine is prepared from 2-hydroxycyclobuta[b]pyridine).

The substituted heterocyclic arylcyclobutane compounds can be used to prepare alkenyl and alkynyl heterocyclic arylcyclobutane monomers. For example, a maleamic acid derivative of cyclobutapyridine can be prepared by contacting 2-aminocyclobutapyridine with maleic anhydride in the presence of a suitable organic solvent, such as chloroform at suitable reaction temperatures. To prepare a monocyclobutapyridine, about equal moles of 2-aminocyclobutapyridine and maleic anhydride are employed. The maleamic acid derivative of cyclobutapyridine can be employed to prepare 2-[N-maleimido]cyclobutapyridine by treating the maleamic acid derivative at suitable reaction temperatures in a suitable organic solvent, for example, sodium acetate in acetic acid. Suitable reaction temperaures include the range of 100° to 120° C.

In another example, 2-bromocyclobutapyridine can be employed to prepare 2-vinylcyclobutapyridines. The bromocyclobutapyridine is contacted with excess ethylene at suitable pressure in the presence of a suitable catalyst system and solvent, and at suitable reaction temperatures. Suitable catalyst systems include palladium (II) acetate; and a suitable cocatalyst is tri-o-tolylphosphine. Suitable solvents include acetonitrile, and suitable reaction temperatures include 125° C.

In yet another example, 2-bromocyclobutapyridine can be employed to prepare a monocyclobutapyridine monomer having a vinyl bridging member connecting the cyclobutapyridine moiety with an organic molecular group, such as an aromatic moiety. For example, to prepare 1-(4-methylphenyl)-2-(2-cyclobutapyridyl)ethene, an amount of 2-bromocyclobutapyridine is contacted with a substantially equal to slightly greater molar amount of 4-methylstyrene in the presence of a suitable catalyst system, in a suitable solvent under suitable reaction conditions. Suitable catalyst systems include palladium (II) acetate and a suitable cocatalyst includes tri-o-tolylphosphine. Suitable solvents include acetonitrile, and suitable reaction conditions include refluxing for a sufficient time.

The monomeric compositions employed in this invention are useful in preparing polymeric compositions wherein the monomers are linked through the arylcyclobutane moieties. Other compositions which can undergo addition polymerization reactions under the ring-opening conditions can be included in the polymeric composition. Preferably, poly(arylcyclobutane) monomers are included. Examples of suitable moieties are other ethylenically unsaturated moieties, acetylenic moieties, and other arylcyclobutane moieties. The arylcyclobutane moiety can undergo simple addition polymerization reactions as well as Diels-Alder-type reactions.

For example, for the benzocyclobutane monomers which undergo simple addition polymerization, structures can form which correspond to the formulae:

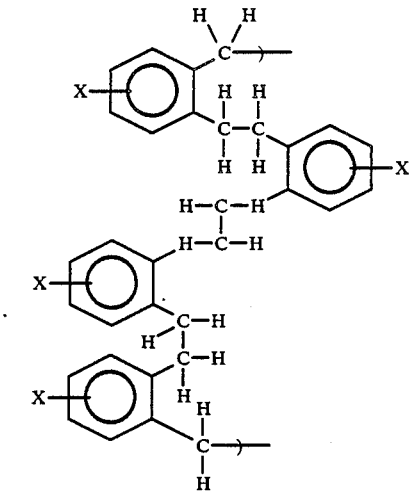

with the latter structure being more prevalent.

For the benzocyclobutane monomers which can undergo Diels-Alder reactions, i.e., the cyclic imide benzocyclobutanes, structures can form which correspond to the formula

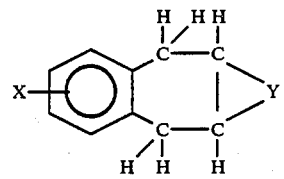

can be provided.

The monomeric compositions of this invention are useful in thermoset resin applications. The cyclobutene ring opens under exposure to radiation, such as gamma-, electron-beam, and thermal radiation to provide addition polymerization sites. Preferably, thermal radiation is employed because it is applied via conventional methods, and can be applied in a variety of ways. Typically, temperatures from about 200° C. to about 300° C. are suitable to open the ring. Somewhat lower temperatures can open the ring when a metal catalyst is employed in the reaction. Suitable metal catalysts include copper salts. Once the ring is open, moieties which can undergo addition polymerization reactions can react at such sites. Typically, other opened cyclobutane rings will react thereto.

In view of the fact that the monomeric compositions of this invention can readily polymerize under thermal radiation conditions, such compositions can be employed in compression molding and transfer molding processes, and as temperature activated adhesives. In compression molding, an amount of the monomeric composition is added to a mold with an effective amount of a suitable mold release agent. The mold is subjected to sufficient temperature and pressure conditions to provide a solid polymer or copolymer part.

The polyarylcyclobutene monomers useful in preparing copolymers of this invention can be prepared according to the method disclosed in U.S. Pat. No. 4,540,763, herein incorporated by reference. Such monomers and prepolymers thereof can be added to the monoarylcyclobutane monomer to affect the properties of the final copolymers. For example, polyarylcyclobutane polymers can have glass transition temperatures of greater than about 300° C. Therefore, such polymers can be added to monoarylcyclobutane monomers which would provide a polymer with a low glass transition temperature to raise the glass transition temperature of that polymer. A preferred polyarylcyclobutane monomer is a bisbenzocyclobutane linked with meta-divinylbenzene units which corresponds to the formula

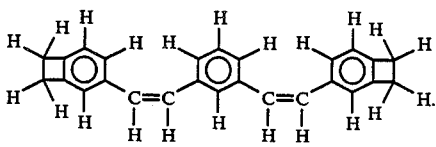

XXVI

The isomers are also preferred.

When copolymerizing divinylbenzene bisbenzocyclobutane with 1-phenyl-2-(4-benzocyclobutyl)ethene, or 1-(4-methylphenyl)-2-(4-benzocyclobutyl)ethene, or 1-(4-tert-butylphenyl)-2-(4-benzocyclobutyl)ethene or 1-(2-naphthyl)-2-(4-benzocyclobutyl)ethene, such copolymers exhibit increased glass transition temperatures and maintain their weight at higher temperatures compared to polymers prepared exclusively from the monobenzocyclobutane monomers.

The polymers and copolymers of this invention can be prepared by subjecting the monomers or comonomer mixtures to sufficient polymerization conditions. Suitable polymerization conditions include subjecting the monomers or comonomers to sufficient polymerization temperaures, to photoinitiate a polymerization in the presence of a suitable photoinitiating catalyst, and the like. Preferably, the polymers are prepared by subjecting the monomers and comonomers to sufficient temperatures. Typically, such temperaures can range from about 150° C. to about 300° C. It may be advantageous to prepare a prepolymer of the monomer or comonomers. A prepolymer can be prepared by subjecting the monomers and comonomers to sufficient polymerization temperatures but for a time insufficient to cure the polymer or prepolymer. Such a process may be desirable to remove any volatiles in the monomer or comonomer mixture which can be present for a variety of reasons, namely due to unreactive starting materials.

The monoarylcyclobutane and polyarylcyclobutane copolymers of this invention are especially versatile. The monoaryl cyclobutanes can impart compression molding capabilities to the substantially rigid thermosetting polyarylcyclobutane polymers. Alternatively, the polyarylcyclobutane monomers can be added to the monoarylcyclobutane monomers to increase the monoarylcyclobutane polymers' glass transition temperatures. Therefore, any ratio of monoarylcyclobutane monomer to polyarylcyclobutane monomer can be employed and can be determined based upon an evaluation of the type of properties desired of the final copolymer.

The versatility of the copolymers of this invention enables such polymers and copolymers to be utilized in many engineering applications. An especially useful application is in the preparation of laminates for printed wiring boards. An especially desirable combination for such laminates is combining 95 parts of 1-(4-methylphenyl)-2-(4-benzocyclobutenyl)ethene with 5 parts of meta-divinylbenzene linked bisbenzocyclobutane. Laminates can be prepared in any conventional manner. For example, a liquid form of the monomer mixture can be provided and then used to impregnate any suitable fibrous material, such as glass fiber mat. The fibers can then be cured by heating to suitable curing temperatures. Alternatively, the monomers can be mixed and combined with suitable reinforcing materials in a random fiber composite process.

The copolymers in this invention can also be used as passivation or planarization resins. A prepolymer form of a suitable comonomer or copolymer mixture can be spin-coated onto a chip.

In transfer molding, an amount of the monomeric composition is melted to a liquid, and then injected into a mold. The mold is at a temperature and under pressure sufficient to polymerize the monomer or comonomers and to provide a solid polymer or copolymer part.

As an adhesive, an amount of the monomeric composition can be coated onto a surface. Advantageously, the monomeric composition is first melted. The second surface to be adhered to the first is then contacted to the coated surface. The pieces can then be subjected to sufficient polymerization conditions to bond the two surfaces together.

Polymeric compositions of this invention exhibit excellent temperature and chemical resistance. They can exhibit glass transition temperatures of greater than 250° C., preferably greater than 300° C., and most preferably greater than 400° C. The polymers also possess high physical strength and durability. The polymeric compositions are highly useful in the electronics industry. Examples of such electronics uses include the preparation of passivation and planarization resins, die attach materials, composites and laminates for providing electronic circuit boards, encapsulation resins for integrated circuits, and the like.

The following examples are illustrative only, and do not limit the scope of the invention.

EXAMPLES

Preparation of Monomers

Preparation 1

1-Phenyl-2-(4-Benzocyclobutyl)ethene Monomer

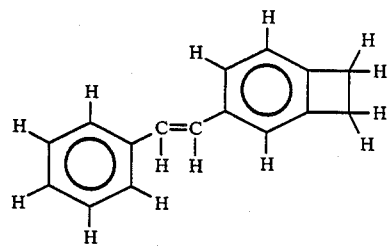

A solution of 2.4 g 4-bromobenzocyclobutane, 1.4 g styrene, 2.4 g tri-n-butylamine, 29 mg palladium (II) acetate, 100 mg of tri-o-tolylphosphine and 10 ml acetonitrile is stirred under nitrogen atmosphere at reflux for three hours. The reaction mixture is poured into 60 ml 10 percent HCl. The product is isolated by filtration, dried, recrystallized in ethanol, and isolated. About 2.10 g of greenish monomer product is prepared.

Preparation 2
4-Decylamido-1-Cyanato Benzocyclobutane Monomer

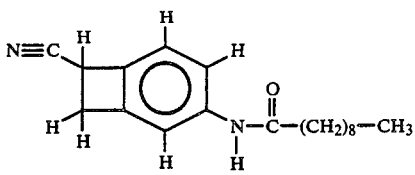

Using a 100 ml 4-necked flask, equipped with reflux condensor and topped with nitrogen outlet, 3.4 g (0.02 moles) of decanoic acid dissolved in 25 ml dried tetrahydrofuran is added by syringe. About 3.2 g (0.02 moles) of 1,1-carboxydimidoazole dissolved in 45 ml of tetrahydrofuran is syringed into the funnel. The mixture is heated to reflux and is allowed to reflux for 4 hours and is then cooled to room temperature. About 3 g of 4-amino-1-cyano-benzocyclobutane in 15 ml of tetrahydrofuran is added to the funnel. The reaction mixture is stirred overnight at room temperature and poured into 300 ml of water and stirred for 30 minutes. The product is extracted 3 times with 150 ml methylene chloride, and the combined methylene chloride extracts are extracted with 3,250 ml portions of 10 percent aqueous hydrochloric acid followed by extractions of 250 ml 10 percent hydrochloric acid, 1 extraction with 250 ml water and two extractions with 250 ml saturated sodium carbonate followed by 2 extractions at 250 ml of water. The product is dried over magnesium sulfate, filtered and recovered. About 5.7 g of a beige-colored solid is obtained.

Preparation 3
1-Cyanato-4-Acetamidobenzocyclobutane Monomer

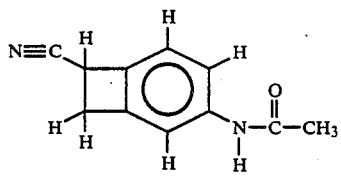

About 4 g (0.02 moles) of 4-amino-1-cyanobenzocyclobutane is placed in a 100 ml flask equipped with an addition funnel, thermometer and nitrogen inlet. Additionally, 3.3 g (0.03 moles) of triethylamine in 60 ml of methylene chloride is added. A solution of acetic anhydride, 3.4 g (0.03 moles) in 5 ml of methylene chloride is added dropwise while keeping the temperature at below 5° C. Once addition is completed, the reaction is allowed to warm to room temperature overnight. The reaction mixture is added to 400 ml of water and stirred with magnetic stirrer and 50 ml of methylene chloride is added to dissolve the gummy solid. The methylene chloride layer is extracted and washed with 200 ml saturated sodium carbonate, 200 ml of water, 200 ml of 10 percent hydrochloric acid and then washed twice with 300 ml of water. The solution is dried over magnesium sulfate, filtered and the solvent is evaporated to yield an off-white solid. The solid is dissolved in a 70:30 volume percent mixture of toluene and ethanol and the product is recrystallized and recovered. The monomer has a melting point of between 163° and 168° C.

Preparation 4
1-(2-Naphthyl)-2-(4-Benzocyclobutyl)ethene Monomer

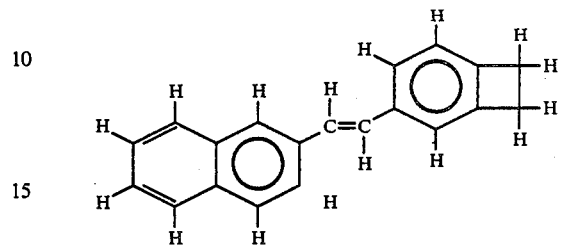

A solution of 3.0 g 4-bromobenzocyclobutane, 2.5 g 2-vinylnaphthalene, 3.0 g tri-n-butylamine, 150 mg tri-o-tolylphosphine, 36 mg palladium (II) acetate, and 10 ml acetonitrile is stirred at reflux under nitrogen atmosphere for 4 hours. The reaction mixture is poured into 60 ml of 10 percent HCl. The product is isolated by filtration, dried, recrystallized from ethanol, and isolated. About 1.8 g of monomer is prepared.

Preparation 5
1-(p-tert-butylphenyl)-2-(4-benzocyclobutenyl)ethene Monomer

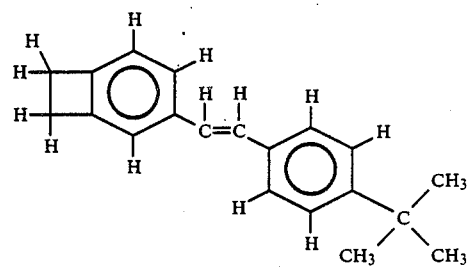

A solution of 3.0 g 4-bromobenzocyclobutane, 2.6 g 4-tert-butylstyrene, 3.0 g tri-n-butylamine, 150 mg tri-o-tolylphosphine, 36 mg palladium (II) acetate, and 10 ml acetonitrile is stirred under nitrogen at reflux for 4 hours. The reaction mixture is poured into 60 ml of 10 percent HCl. The product is isolated by filtration, dried, recrystallized from ethanol, and isolated. About 1.8 g of monomer is prepared.

Preparation 6
1-(4-methylphenyl)-2-(4-benzocyclobutenyl)ethene Monomer

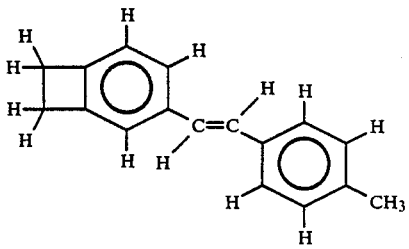

A solution of 3.0 g 4-bromobenzocyclobutane, 1.9 g 4-methylstyrene, 3.0 g tri-n-butylamine, 150 mg tri-o- tolylphosphine, 36 mg palladium (II) acetate, and 10 ml of acetonitrile is stirred at reflux under nitrogen for 4 hours. The reaction mixture is poured into 60 ml of 10 percent HCl. The product is isolated by filtration, dried, recrystallized from ethanol, and isolated. About 2.9 g of monomer is prepared.

Preparation 7

Meta-DivinylBenzene Linked Bisbenzocyclobutane Monomer

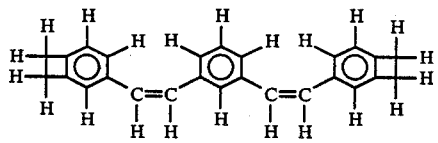

A 25 ml flask equipped with a reflux condensor and nitrogen inlet is charged with 1.5 g (0.008 moles) of 4-bromobenzocyclobutane and 0.5 g (0.004 moles) of meta-divinylbenzene, 1.8 g of tri-n-butylamine 62 mg tri-o-tolyphosphene 18 mg of palladium (II) acetate, and 5 ml of acetonitrile. The reaction mixture is heated to reflux under nitrogen for 4 hours. The mixture is cooled to room temperature and stirred into 60 ml of 10 percent hydrochloric acid. The precipitate is collected by filtration, washed with water and air dried. The dried precipitate is then dissolved in 100 ml of boiling toluene filtered hot and cooled to yield 830 mg of the monomer. The monomer has a melting point of between 150° and 152° C.

Preparation 8

Preparation of N-[5-(1-Cyanobenzocyclobutyl)]Maleimide Monomer

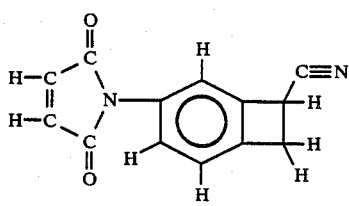

Into a 250 ml, 3-necked flask equipped with mechanical stirrer, reflux condenser, thermometer and nitrogen inlet is placed 11 g (0.045 moles) of N-[5-(1-cyanobenzocyclobutyl)]maleamic acid, 2.4 g (0.03 moles) of anhydrous sodium acetate, and 45.94 g (0.765 mole) of fresh glacial acetic acid. The mixture is stirred and slowly heated under nitrogen until a clear yellow solution results (at about 117° C. and 118° C.). After 5 minutes, the heat is removed and the reaction mixture is allowed to cool under nitrogen overnight at room temperature. It is then slowly poured into a vigorously stirred slurry of ice and water (120 g total), and the resulting yellow precipitate filtered, washed with water until neutral to litmus, and transferred to a 500 ml beaker containing 150 ml of aqueous saturated sodium bicarbonate. This mixture is stirred for 10 minutes, then 150 ml of chloroform is added and stirred for an additional 10 minutes. The organic layer is taken up in three 50 ml portions of chloroform, and the solutions are combined and washed once with 150 ml of water. The chloroform solution is dried over anhydrous magnesium sulfate, filtered and evaporated on a rotary evaporator to give a viscous yellow oil. The product is pumped under vacuum overnight to give a yellow solid which is purified by column chromatography on silica gel using 70 percent toluene, 30 percent ethyl acetate as the eluent. The yield is 5.7 g equal to about 56.5 percent of theoretical. The melting point is between about 55° C. and 60° C.

Example 1

Polymerization of 1-Phenyl-2-(4-Benzocyclobuty)ethene 160 mg of the monomer prepared in Preparation 1 is placed in a pyrex test tube fitted with a nitrogen inlet. The test tube is placed into a 170° C. Wood's metal bath. The bath temperature is raised to 250° C. over approximately 10 minutes. The temperature is maintained at 250° C. for 60 minutes, and then the tube containing the reaction product is removed from the bath and cooled to room temperature. The product is a yellowish clear polymer, and is removed from the tube by a patula. The polymer is insoluble in chloroform. The glass transition temperature in nitrogen is 220° C.

Example 2

Polymerization of 4-Dodecylamido-1-Cyano-Benzocyclobutane 0.5 g of the monomer prepared in Preparation 2 is dissolved in 2 ml of methylene chloride, and the solution is spread on a steel plate in an air oven. The plate and solution are heated at 250° C. for one hour. The black polymer is glossy, softens between 153° C. and 160° C. and is slightly soluble in methyl chloride.

Example 3

Polymerization of 1-Cyano-4-Acetamido-Benzocyclobutane

A sample of 0.5 g of the monomer prepared in Preparation 3 is placed in a test tube and heated for 30 minutes at 200° C. under vacuum. A tan powder is formed. A second sample of the monomer is placed in a test tube and heated for three hours at 250° C. A shiny black powder is formed.

Example 4

Polymerization of 1-(2-Naphthyl)-2-(4-Benzocyclobutyl)ethene

One hundred and fifty milligrams of the monomer prepared in Preparation 4 are placed in a test tube and immersed in a Wood's metal bath at 170° C. After the monomer melts, the temperature is raised to 200° C. for one hour, then to 220° C. for one hour, and then to 250° C. for three hours. The tube is then cooled to room temperature and the polymer is removed. The polymer has a glass transition temperature of 220° C.

Example 5

Polymerization of 1-(p-tertbutylphenyl)-2-(4-Benzocyclobutyl)ethene

The monomer prepared in Preparation 5 is polymerized in the same manner as described in Example 4. The polymer has a glass transition temperature of 218° C.

Example 6

Polymerization of 1-(para-methylphenyl)-2-(4-Benzocyclobutyl)ethene

The monomer prepared in Preparation 6 is polymerized in the same manner as described in Example 4. The polymer has a glass transition temperature of 221° C.

Example 7

Copolymers of Divinylbenzene Linked Bisbenzocyclobutane and Monobenzocyclobutane Monomers A: Copolymers of 1-(2-Naphthyl)-2-(4-Benzocyclobutyl)ethene Copolymers of the monomer prepared in Preparation 4 and Preparation 7 are prepared with different ratio of the monomers. The desired ratio of the monomers weighing a total of 150 mg is placed in a test tube fitted with a nitrogen inlet and immersed in a Wood's metal bath at 170° C. When the monomer mixture has melted, the temperature is raised to 200° C. and maintained for one hour; the temperature is then raised to 220° C. and held for one hour. The temperature is then raised to 250° C. for three hours. The tube is removed from the bath, cooled to room temperature and the copolymer sample is removed. Thermal data for the copolymers are provided in Table I.

TABLE I

| Percent Monomer #4 | Percent Monomer #7 | Tg °C.[a] | Weight Loss °C.[b] 0% | 5% |
|---|---|---|---|---|
| 99 | 1 | 240 | 400 | 420 |
| 98 | 2 | 246 | 400 | 420 |
| 95 | 5 | 263 | 410 | 440 |
| 90 | 10 | 265 | 410 | 450 |
| 85 | 15 | 280 | 425 | 450 |
| 75 | 25 | 310 | 440 | 450 |
| 50 | 50 | 350[c] | — | — |

[a]Determined by DSC at 5° C. per minute scan rate.
[b]Determined by TGA in air at 10° C. per minute scan rate. 0 percent is the onset of weight loss.
[c]DSC shows no transition up to 350° C.

B: Copolymers with 1-Phenyl-2-(4-Benzocyclobutyl)ethene

Ten weight percent of the monomer prepared in Preparation 7 is copolymerized with 90 weight percent of the monomer prepared in Preparation 1. The copolymer is prepared in the same manner as the copolymers in A above. The copolymer has a glass transition temperature of 257° C.

C: Copolymers with 1-(p-methylphenyl)-2-(4-Benzocyclobutyl)ethene

Two samples of a copolymer of the monomer prepared in Preparation 6, and the monomer of Preparation 7 are prepared. The process used in A above is used to prepare the polymers. Sample 1 has 15 weight percent monomer 7 and 85 weight percent of monomer 6. The copolymer has a glass transition temperature of 250° C. Sample 2 has 25 weight percent monomer 7, and 75 weight percent monomer 6. The copolymer has a glass transition temperature of 282° C.

D: Copolymers with 1-(p-tertbutylphenyl)-2-(4-Benzocyclobutyl)ethene

Fifteen weight percent of monomer 7 is copolymerized with 85 weight percent of the monomer of Preparation 5, in the manner employed in A above. The copolymer has a glass transition temperature of 276° C.

Example 8

Polymerization of N-[5-(1-cyanobenzocyclobutyl)]maleimide

Into a 25-ml, two-necked flask equipped with a reflux condenser, nitrogen inlet and magnetic stir bar is placed 0.5 g (2.2 mmole) of the monomer prepared in Preparation 8 and 15 ml of mesitylene. The mixture is purged with nitrogen and heated with stirring. Initially, all of the maleimide derivative dissolves to give a clear yellow solution. Upon reaching reflux, the solution becomes cloudy and a beige powder precipitates. Ager 2 hours of reflux, the reaction is cooled and the precipitated polymer is filtered off and washed free of residual mesitylene with chloroform and dried. The yield is quantitative.

Example 9

Polymerization of N-[5-(1-cyanobenzocyclobutyl)]maleimide

Into a 25-ml, one-necked, round-bottomed flask equipped with a nitrogen inlet is placed 0.1 g (0.446 mmole) of the monomer prepared in Preparation 8. The flask is purged with nitrogen and immersed in an oil bath. The bath temperature is raised to 200° C. over 1 hour. After heating at 200° C. for 20 minutes, the melted monomer solidifies to a pale yellow transparent solid. The flask is cooled and the polymer removed by breaking it up with a spatula. The yield is quantitative.

Example 10

Compression Molding of Copolymers

A copolymer of 95 weight percent 1-(2-naphthyl)-2-(4-benzocyclobutenyl)ethene, monomers 4 and 5 weight percent of divinylbenzene linked bisbenzocyclobutane, monomer 7, is compression molded. A 0.6 g sample of the monomer mixture is placed in a rod mold bore of 0.5 inches. Pistons on both sides of the sample are used to compress the sample. A heater band is used to heat the sample slowly to 200° C., and then the temperature is raised over 30 minutes to 250° C. A pressure of 1,000 pounds force is applied to the pistons. The mold temperature is raised to 265° C. and 5 tons force is applied. The temperature is maintained for 5 minutes, and then is raised to 275° C. for 5 minutes. The mold is cooled to room temperature, while the pressure is maintained. The pistons are removed, and the clear, dark amber copolymer piece is recovered.

What is claimed is:

1. A polymeric composition comprising, in polymerized form, a monomer represented by the formula:

$$(R^3)_2-C=C-(R^1)_n-Ar\left(\begin{matrix}CR_2\\|\\CR_2\end{matrix}\right)_m$$
$$\overset{|}{R^2}$$

wherein
Ar is an aryl moiety;
R, $R^2$ and $R^3$ are separately and independently in each occurrence hydrogen, an electron-donating moiety or an electron-withdrawing moiety, provided at least one $R^3$ is an aryl moiety;

$R^1$ is a polyvalent organic moiety or a polyvalent inorganic moiety;

m is an integer of at least 1; and n is an integer of zero or 1.

2. The polymeric composition of claim 1 wherein the monomer corresponds to the formula:

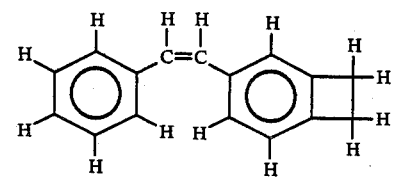

3. The polymeric composition of claim 1 wherein the monomer corresponds to the formula:

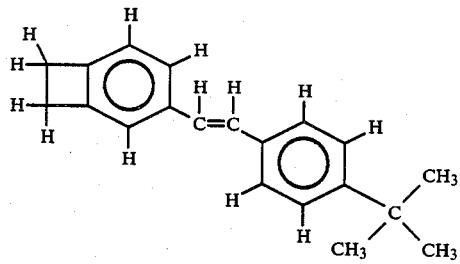

4. The polymeric compositon of claim 1 wherein the monomer corresponds to the formula:

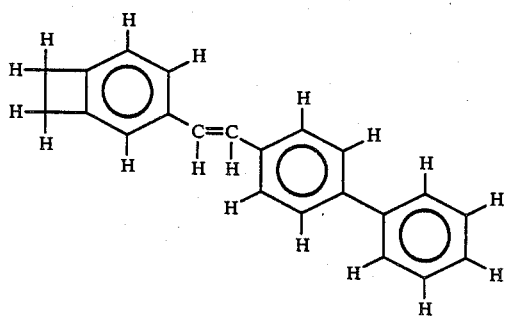

5. The polymeric composition of claim 1 wherein the monomer corresponds to the formula:

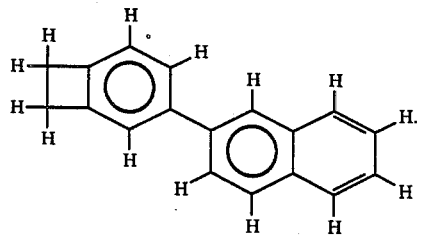

6. The polymeric composition of claim 1 wherein the monomer corresponds to the formula:

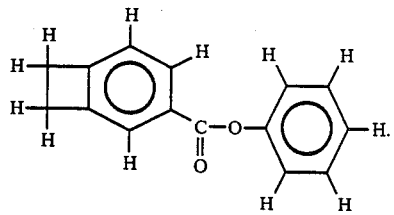

7. The polymeric composition of claim 1, wherein the monomer is 1-(2-naphthyl)-2-(4-benzocyclobutyl)ethene, which corresponds to the formula

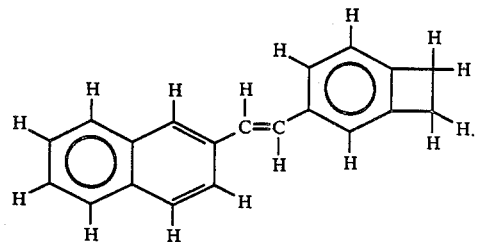

8. The polymeric composition of claim 7, comprising a reaction product of the monomer, and a second monomer which contains at least two reactive arylcyclobutane moieties.

9. The polymeric composition of claim 8, wherein the second monomer is a meta-divinylbenzene linked bis-benzocyclobutane, which corresponds to the formula

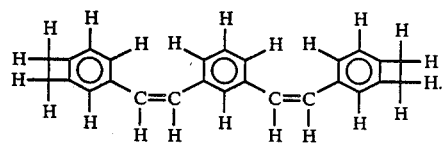

10. The polymeric composition of claim 1 wherein the monomer corresponds to the formula:

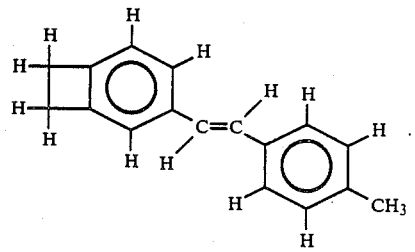

11. A polymeric composition comprising, in polymerized form, a monomer represented by the formula:

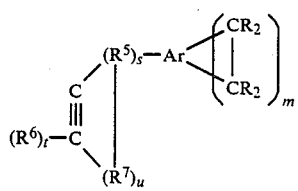

wherein

Ar is an aryl moiety;

R and $R^6$ are separately and independently in each occurrance hydrogen, an electron-donating moiety, or an electron-withdrawing moiety;

$R^5$ and $R^7$ are a polyvalent organic moiety, or a polyvalent inorganic moiety;

m is an integer of at least 1;

s is an integer of zero or 1;

t is an integer of zero or 1; and u is an integer of zero or 1; provided that when s is zero then the alkynyl group is bonded directly to the aryl moiety, u is zero and t is 1; when t is 1, then u is zero; and when u is 1, then s is 1, and t is zero.

12. The polymeric composition of claim 11, wherein u is 0, t is 1 and the monomers correspond to the formula

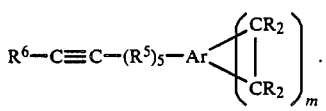

13. The polymeric composition of claim 12, wherein the aryl moiety is a benzene moiety, and m is 1.

14. The polymeric composition of claim 13 wherein the monomer corresponds to the formula:

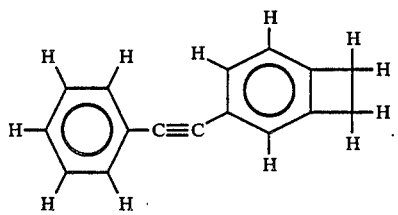

15. A polymeric composition comlprising, in polymerized form, a monomer represented by the formula:

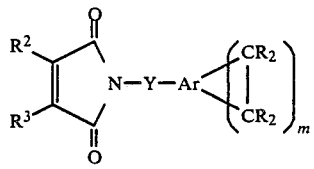

wherein

Ar is an aromatic moiety;

R is separately in each occurrence hydrogen or an electron-withdrawing group;

$R^2$ and $R^3$ are separately in each occurrence hydrogen, a hydrocarbyl, hydrocarbyloxy or hydrocarbylthio group;

Y is a direct bond or a divalent organic moiety; and m is an integer of at least 1.

16. Th polymeric composition of claim 15 wherein the monomer corresponds to the formula:

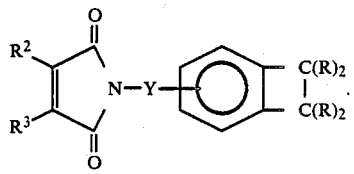

17. A polymeric composition comprising a reaction product of (a) a monoarylcyclobutane monomer containing one reactive arylcyclobutane moiety, wherein the arylcyclobutane moiety is an aryl group which contains one or more cyclobutane rings fused to the aromatic ring, and (b) a second monomer which contains at least two reactive arylcyclobutane moieties.

18. The polymeric composition of claim 17 wherein the monoarylcyclobutane monomer is represented by the formula:

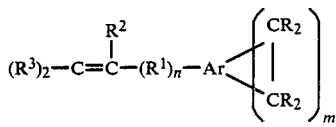

wherein

Ar is an aryl moiety;

R, $R^2$ and $R^3$ are separately and independently in each occurrence hydrogen, an electron-donating moiety or an electron-withdrawing moiety;

$R^1$ is a polyvalent organic moiety or a polyvalent inorganic moeity;

m is an integer of at least 1; and n is an integer of zero or 1.

* * * * *

UNITED STATES PATENT AND TRADEMARK OFFICE
CERTIFICATE OF CORRECTION

PATENT NO. : 4,783,514
DATED : November 8, 1988
INVENTOR(S) : Robert A. Kirchhoff et al It is certified that error appears in the above-identified patent and that said Letters Patent is hereby corrected as shown below:

Column 1, line 28, "structural" should read --structure--
Column 2, line 19, "monoarylcyclobutenes" should read --monoarylcyclobutanes--
Column 5, line 22, "arylcyclobutene" should read --arylcyclobutane--
Column 9, line 13, "XXI;" should read --XXII;--
Column 12, line 46, "cyclobutene" should read --cyclobutane--
Column 13, line 3, "polyarylcyclobutene" should read -- polyarylcyclobutane--
Column 14, line 5, "(4-benzocyclobutenyl) should read
                                      --(4-benzocyclobutyl)--
Column 15, line 20, "1,1-carboxydimidoazole" should read
                                      --1,1-carbonyldiimidazole--
Column 16, line 29, "(4-benzocyclobutenyl)" should read
                                      --(4-benzocyclobutyl)--
Column 16, line 53, "(4-benzocyclobutenyl)" should read
                                      --(4-benzocyclobutyl)--
Column 18, line 11, "(4-Benzocyclobuty)" should read
                                      --(4-Benzocyclobutyl)--
Column 18, line 21, "patula" should read --spatula--
Column 20, line 38, "(4-benzocyclobutenyl)" should read
                                      --(4-benzocyclobutyl)--
Claim 15, Column 23, line 37, "comlprising" should read --comprising--
Claim 16, Column 24, line 10, "Th" should read --The--

Signed and Sealed this

Twenty-ninth Day of May, 1990

Attest:

HARRY F. MANBECK, JR.

Attesting Officer

Commissioner of Patents and Trademarks